(12) United States Patent
Thomas et al.

(10) Patent No.: US 11,241,368 B1
(45) Date of Patent: Feb. 8, 2022

(54) SMART PACIFIER THAT PERFORMS FUNCTIONS BY WIRELESS CONNECTION TO A COMPUTING DEVICE AND APPLICATION

(71) Applicants: LaToya Shontay Thomas, Copperas Cove, TX (US); Larry Anthony-Quinn Thomas, Copperas Cove, TX (US)

(72) Inventors: LaToya Shontay Thomas, Copperas Cove, TX (US); Larry Anthony-Quinn Thomas, Copperas Cove, TX (US)

( * ) Notice: Subject to any disclaimer, the term of this patent is extended or adjusted under 35 U.S.C. 154(b) by 306 days.

(21) Appl. No.: 16/661,916

(22) Filed: Oct. 23, 2019

Related U.S. Application Data

(60) Provisional application No. 62/749,215, filed on Oct. 23, 2018.

(51) Int. Cl.
*H04W 4/80* (2018.01)
*A61J 17/00* (2006.01)
*A61B 5/03* (2006.01)
*A61B 5/00* (2006.01)

(52) U.S. Cl.
CPC ............. *A61J 17/103* (2020.05); *A61B 5/038* (2013.01); *A61B 5/746* (2013.01); *A61J 17/1011* (2020.05); *A61J 17/1012* (2020.05); *H04W 4/80* (2018.02); *A61J 2200/72* (2013.01)

(58) Field of Classification Search
CPC ...................................... A61J 17/103
See application file for complete search history.

(56) References Cited

U.S. PATENT DOCUMENTS

| 6,066,161 | A | * | 5/2000 | Parella | ..................... | A61J 17/10 |
| | | | | | | 606/234 |
| 2017/0020788 | A1 | * | 1/2017 | Malone | ................ | A61J 17/1111 |
| 2018/0064612 | A1 | * | 3/2018 | Coleman | .............. | A61J 17/1011 |
| 2019/0314250 | A1 | * | 10/2019 | Wood | ................... | A61J 17/1012 |
| 2020/0390659 | A1 | * | 12/2020 | Maitre | .................... | G06F 3/165 |

\* cited by examiner

*Primary Examiner* — Joseph H Feild
*Assistant Examiner* — Pameshanand Mahase
(74) *Attorney, Agent, or Firm* — Plager Schack LLP; Mark H. Plager; Stephen Hallberg

(57) ABSTRACT

A smart pacifier that performs various functions via smart device connection and application is disclosed. In all of its iterations, there is the ability to put the parent in Bluetooth or other iteration of wireless connection with the pacifier so that each of the features of the pacifier can be accessed through a smart device application, permitting each of them to be operated while the parent is out of sight of the child, and for the pacifier to shut down remotely based on direct sensory interaction with the child.

10 Claims, 6 Drawing Sheets

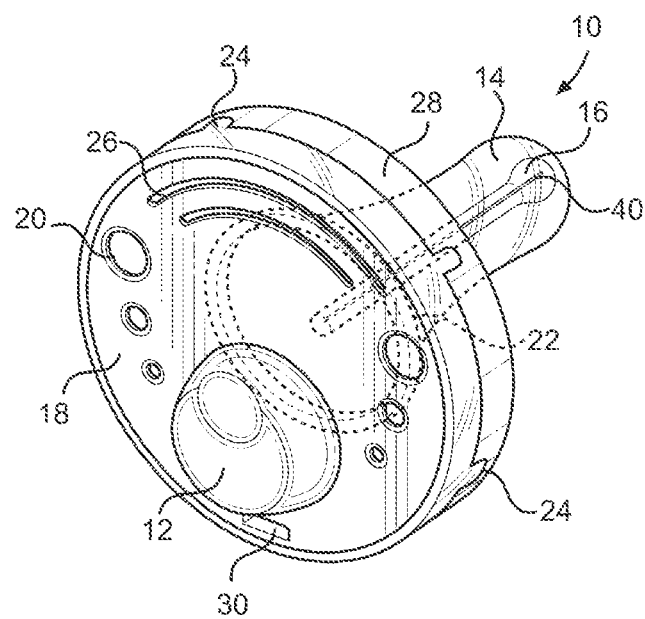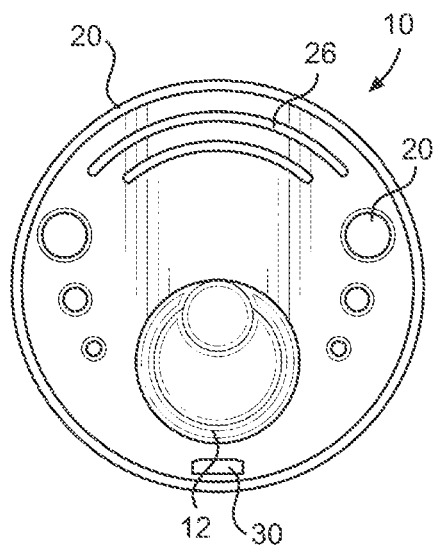
FIG. 4    FIG. 5
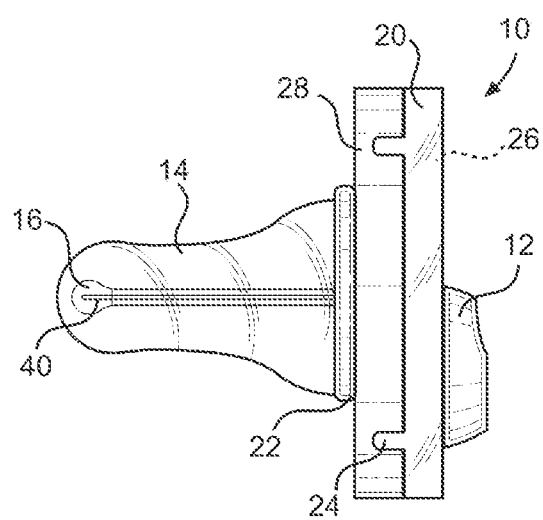
FIG. 6

SMART PACIFIER THAT PERFORMS FUNCTIONS BY WIRELESS CONNECTION TO A COMPUTING DEVICE AND APPLICATION

CLAIM OF BENEFIT TO PRIOR APPLICATION

This application claims benefit to U.S. Provisional Patent Application 62/749,215, entitled "A Lullaby pacifier," filed Oct. 23, 2018. The U.S. Provisional Patent Application 62/749,215 is incorporated herein by reference.

BACKGROUND

Embodiments of the invention described in this specification relate generally to baby pacifiers, and more particularly, to a smart pacifier that performs functions by wireless connection to a computing device and application.

Babies cry when needing any of several things: teething comfort, audible comforting sounds, visual stimulation, and other types of stimulation. Currently, pacifiers are used to calm crying babies. However, pacifiers get lost and are often not able to be located. Parents sometimes need to be out of sight of a baby but still need access to baby monitoring. Baby toys may keep a baby momentarily occupied, but baby toys are generally not sensitive to a baby's state (e.g., crying, sleeping, calm, etc.). Furthermore, most baby toys cannot shut off automatically.

Smart electronic devices are plentiful in the market today. However, conventional pacifiers currently in the market do not incorporate any smart electronic features. None of the existing conventional pacifiers have the ability for smart device connection, and do not provide smart device-type interaction options between the child and parents or guardians.

Therefore, what is needed is a way to incorporate smart device-type features into a pacifier with wireless and remote access to the operation of those features in order to interact with babies, soothe crying babies, stimulating and entertaining babies, and other interactions.

BRIEF DESCRIPTION

A novel smart pacifier is disclosed that performs functions by wireless connection to a computing device and an application running on the computing device. In some embodiments, the smart pacifier is able to put a parent in wireless connection with the smart pacifier so that each of the features of the pacifier can be accessed through a smart device application, permitting each of them to be operated while the parent is out of sight of the child, and for the pacifier to shut down remotely based on direct sensory interaction with the child. In some embodiments, the smart pacifier connects wirelessly to a computing device with an application which allows a user of the computing device to control features and functions being performed by the smart pacifier, and provides other opportunities for interaction with the baby. In some embodiments, the smart pacifier provides a comprehensive array of features, functions, and interaction options including lights, sounds, recording, tracking, wireless-based interactive opportunities, and other interactions between parents, guardians, or other familiar people and the baby, who is in possession of the pacifier and who may be at a nonverbal stage of development. In this way, entertaining a baby who is using the smart pacifier can be performed according to user selection of playing soothing music for the baby to hear, displaying relaxing lights for the baby to see, playing a recording of a familiar voice such as a parent's voice, reading stories to the baby, and talking to the baby through the smart pacifier from the computing device.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 4 conceptually illustrates a perspective view of a smart pacifier in a second form that performs functions by wireless connection to a computing device and application in some embodiments.

FIG. 5 conceptually illustrates a front view of the smart pacifier in the second form that performs functions by wireless connection to a computing device and application in some embodiments.

FIG. 6 conceptually illustrates a side view of the smart pacifier in the second form that performs functions by wireless connection to a computing device and application in some embodiments.

DETAILED DESCRIPTION

Figure 1:
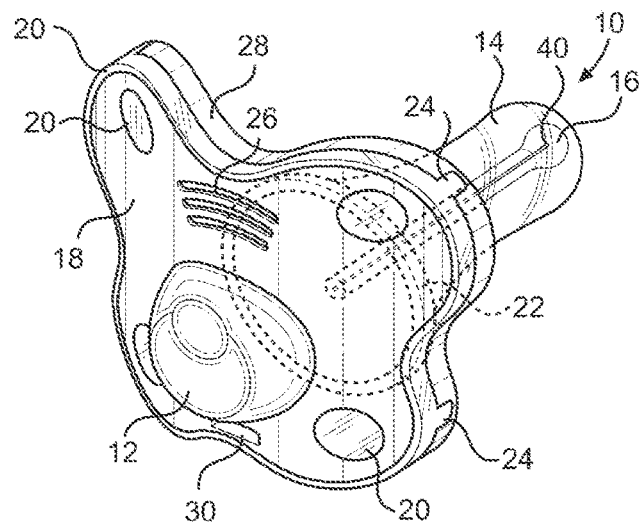
FIG. 1 conceptually illustrates a perspective view of a smart pacifier in a first form that performs functions by wireless connection to a computing device and application in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel smart pacifier that performs functions by wireless connection to a computing device and an application running on the computing device. In some embodiments, the smart pacifier is able to put a parent in wireless connection with the smart pacifier so that each of the features of the pacifier can be accessed through a smart device application, permitting each of them to be operated while the parent is out of sight of the child, and for the pacifier to shut down remotely based on direct sensory interaction with the child.

In some embodiments, the smart pacifier connects wirelessly to a computing device with an application which allows a user of the computing device to control features and functions being performed by the smart pacifier, and provides other opportunities for interaction with the baby. In some embodiments, the smart pacifier provides a comprehensive array of features, functions, and interaction options including lights, sounds, recording, tracking, wireless-based interactive opportunities, and other interactions between parents, guardians, or other familiar people and the baby, who is in possession of the pacifier and who may be at a nonverbal stage of development. In this way, entertaining a baby who is using the smart pacifier can be performed according to user selection of playing soothing music for the baby to hear, displaying relaxing lights for the baby to see, playing a recording of a familiar voice such as a parent's voice, reading stories to the baby, and talking to the baby through the smart pacifier from the computing device.

All the features and functions can be accessed by the user of the computing device who is able to control, select, adjust, create, and otherwise interact with the baby via the smart pacifier, whether the user is interacting with the application running on the computing device while being physically nearby the baby or while being remotely located. In some embodiments, the smart pacifier shuts down automatically and remotely based on direct sensory interaction with the baby.

As stated above, pacifiers are often used to soothe babies who may need something and express by crying. However, pacifiers get lost and are not able to be located and parents cannot always be in sight of a baby since parents sometimes need to be out of sight. Yet, those parents still need access to monitoring, which conventional pacifiers do not offer. Embodiments of the smart pacifier described in this specification solve such problems by maintaining parental connection to the baby even when out of sight via Bluetooth or other wireless technology. Teething babies need gum stimulation which is accomplished through the device's sensors and gyros. Upset babies need audible or visual stimulation, which is provided through the programmable sound system in the pacifier and the lights, which can be timed and/or controlled through programming. The distance "out of sight" matter is accomplished by control via a smartphone application. Power loss is controlled via auto-shut off features. Lost pacifier problems are addressed via tracking features.

Embodiments of the smart pacifier described in this specification differ from and improve upon currently existing options. In particular, some embodiments differ by being able to entertain a baby/child and give them soothing music and relaxing lights. An application or mobile app is provided for computing device use so that parents can record audio of a baby/child via via mic embedded within the smart pacifier, read stories to the baby/child through speakers of the smart pacifier, or just speak to the baby/child to soothe and comfort him or her. The mobile app allows the parent to control functions and features of the smart pacifier via smart phone or tablet computing device, while the software application implementation may be a desktop application or a web-based application which the parent can access via computing device (e.g., desktop computer, laptop, etc.) and connect to the smart pacifier via wireless (e.g., Bluetooth, WiFi, etc.). The parent can also remove the back part of the smart pacifier for the baby/child to enjoy without the smart functions/features, such as the lights, sounds, and/or vibrations. The smart pacifier also includes an auto-shut off, so when the baby is no longer sucking the pacifier, shutdown will be triggered automatically to save battery life.

In addition, some embodiments of the smart pacifier improve upon the currently existing options by because conventional pacifiers in the market do not have stimulating, entertaining, visual and/or audio features and functions, and are not controlled via wireless connection to mobile device or other computing device running the application. In essence, there is no other smart pacifier or other comparable device in the market. For instance, nothing in the existing conventional pacifier market provides sound that is customizable to the degree of uploading particular music, voice recording, or realtime wireless communication from a parent at a smart computing device through the speakers of the smart device to the baby. None of the existing pacifiers provide vibration that can be customized to the degree of setting various rates/rhythms to a pacifier. None of the conventional pacifiers can check for baby temperature and send an alert when a high temperature is detected. Furthermore, there is no way for conventional pacifiers to connect to a smart device application comprehensively so that it can be tracked and utilized. In contrast, the smart pacifier of the present disclosure provides all these features and more.

The smart pacifier of the present disclosure may be comprised of the following elements. This list of possible constituent elements is intended to be exemplary only and it is not intended that this list be used to limit the smart pacifier of the present application to just these elements. Persons having ordinary skill in the art relevant to the present disclosure may understand there to be equivalent elements that may be substituted within the present disclosure without changing the essential function or operation of the smart pacifier.

1. Pacifier for a baby/child to suck on. The pacifier looks like a standard pacifier on the outside, and has the same feel for the baby as a standard pacifier. Examples of pacifier design for the smart pacifier described in this specification are demonstrated in FIGS. 1-6. However, a person of ordinary skill in the relevant art would appreciate that the smart pacifier can work for any of several other pacifier designs beyond those demonstrated in FIGS. 1-6.

2. Wireless/Bluetooth output speaker is a small speaker for the music/voice recording and for volume control. The wireless/Bluetooth output speaker can be used with smart computing device connections where the application (mobile app) is running.

3. LED lights in and around the pacifier which the baby/child can see for entertainment or for basic visual stimulation. The LED lights in and around the pacifier can be connected with smart computing device connectivity to the application.

4. Inside vibration via a vibration ring that provides a tactile feature for soothing and relaxing the baby, and is especially relevant for a teething baby/child. Vibrations can be programmed and controlled with the smart computing device application.

5. Pressure sensor and power module for automatic shut-off by pressure sensitive detection of decompression/non-sucking on pacifier. The power module can be remotely controlled via the application running on the smart computing device (overriding the pressure sensor as a power on/off trigger for the smart pacifier). A decompression electro-mechanical device is inside the smart pacifier for detection of decompression, in order to control automatic shutoff of the smart pacifier when the baby/child is not sucking on the pacifier. The smart pacifier can be pre-set for various shut-off times via the application running on the smart computing device.

6. Power toggle button that connects to underlying power module of the smart pacifier and allows manual shutdown or power up and automatic shut off and on. The power toggle button allows manual (human) control of the shut down and powering up of the smart pacifier (overriding pressure sensor as a power on/off trigger for the smart pacifier). The power toggle button and power module for the powered smart pacifier includes a battery power assembly.

7. Charger that powers the smart pacifier and which can be used to recharge the smart pacifier through a plug connection or wireless recharging and can be controlled remotely via the application running on the smart computing device.

8. Voice recorder that allows the smart pacifier to capture baby verbalizations, crying, cooing, and/or other sounds in and around the baby. The voice recorder captures sound through speakers and is controlled to work via the application running on the smart computing device.

9. Control vibration for soothing the baby/child via remote control of the application running on the smart computing device.

10. Application (software or mobile app) that controls volume, lights, vibration, music and runs on any of several different types of computing devices with wireless connectivity, such as Bluetooth-capable devices. Examples of computing devices include, without limitation, mobile devices, smart phones, tablet computing devices, desktop computers, laptop computers, etc.

11. A removable front pacifier panel that can be detached from physical front side of pacifier to access the inner temperature and pressure sensor, and thereby replace, change, or update the inner temperature and pressure sensor for different or extra vibration features of the smart pacifier to be changed out and/or the front of the pacifier that houses the features to be replaced.

12. An oscillating circuit board that is embedded within the smart pacifier and which controls logic flow for operation of the features and functions of the smart pacifier and information flow to and from the smart computing device.

By way of example, FIG. 1 conceptually illustrates a perspective view of a smart pacifier 10 in a first form that performs functions by wireless connection to a computing device and application. As shown in this figure, the smart pacifier 10 in the first form includes a power toggle button 12, a pacifier nipple 14, a temperature and pressure sensor component assembly 16 with a high temperature alert device 40, a removable front pacifier panel 18, a plurality of lights 20, a vibrating ring 22, a plurality of clips 24, speakers and microphone 26, a back pacifier panel 28, and USB charging port 30.

The power toggle button 12 connects to an underlying power module of an oscillating circuit board of the smart pacifier and provides automatic shut off while also allowing manual shutdown or power up. The pacifier nipple 14 is an orthodontic silicone nipple that is either flat or round. In some embodiments, the temperature and pressure sensor component assembly 16 includes a temperature sensor (or thermometer) that measures internal temperature of the baby/child using the smart pacifier. In some embodiments, the temperature and pressure sensor component assembly 16 includes the high temperature alert device 40 that triggers an alert when the internal temperature of the baby/child is measured at or above a threshold temperature. The temperature and pressure sensor component assembly 16 also includes a decompression/compression sensor that detects when the baby/child is actively sucking on the pacifier nipple 14. In some embodiments, the plurality of lights 20 includes a light ring that surrounds a perimeter of the removable front pacifier panel 18 and several panel lights that shine out of the removable front pacifier panel 18. In some embodiments, the speakers and microphone 26 include Bluetooth speakers operate via a low energy integrated micro-controller to play music and record sound in and around the baby/child using the smart pacifier 10. In some embodiments, several components are embedded within an assembly of the back pacifier panel 28 and the pacifier nipple 14, including at least the temperature and pressure sensor component assembly 16 and an oscillating circuit board (not shown in this figure, but which is described below, by reference to FIGS. 9 and 10). In some embodiments, the vibrating ring 22 is also embedded within the assembly of the back pacifier panel 28 and the pacifier nipple 14. In some embodiments, the USB charging port 30 includes a receptacle for a USB cord to connect to and charge the smart pacifier 10.

Figure 2:
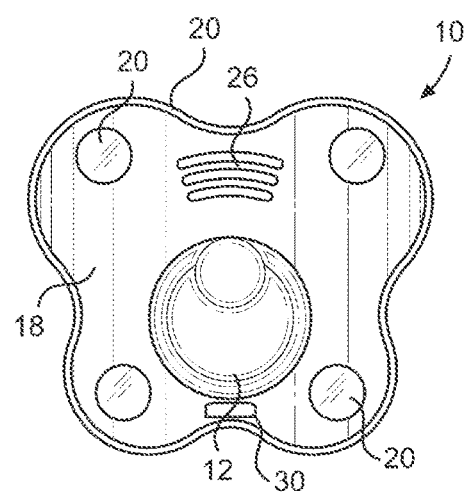
FIG. 2 conceptually illustrates a front view of the smart pacifier in the first form that performs functions by wireless connection to a computing device and application in some embodiments.

Demonstrating another view, FIG. 2 conceptually illustrates a front view of the smart pacifier 10 in the first form that performs functions by wireless connection to a computing device and application. As shown in this figure, the smart pacifier 10 in the first form is a butterfly design. Typically, this form of pacifier is a bigger pacifier that may not be suitable for infants, but is used generally among babies/children who have developed enough to handle the form.

Figure 3:
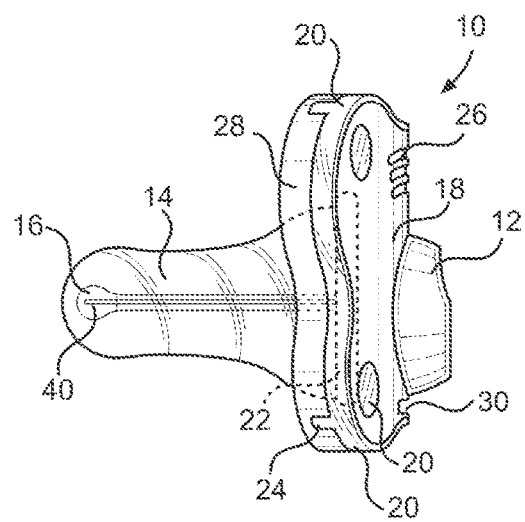
FIG. 3 conceptually illustrates a side view of the smart pacifier in the first form that performs functions by wireless connection to a computing device and application in some embodiments.

In yet another view, FIG. 3 conceptually illustrates a side view of the smart pacifier 10 in the first form that performs functions by wireless connection to a computing device and application. In this side view, the smart pacifier 10 in the first form is demonstrated to have slight curvature in the removable front pacifier panel 18 and the back pacifier panel 28. As a result, the light ring in the plurality of lights 20, the speakers and microphone 26, and the power toggle button 12 are all designed to accommodate the slight curvature shown here. Although the smart pacifier 10 in the first form is shown in this figure with the slight curvature, a person having ordinary skill in the relevant art would appreciate that the smart pacifier 10 can be designed and manufactured without any curvature along the removable front pacifier panel 18 and back pacifier panel 28. An example of a flat design for the removable front pacifier panel 18 and back pacifier panel 28 is demonstrated in a smart pacifier 10 described below, by reference to FIGS. 4-6.

By way of example, FIG. 4 conceptually illustrates a perspective view of a smart pacifier 10 in a second form that performs functions by wireless connection to a computing device and application. As shown in this figure, the smart pacifier 10 in the second form includes the power toggle button 12, the pacifier nipple 14, the temperature and pressure sensor component assembly 16 with the high temperature alert device 40, a removable front pacifier panel 18, a plurality of lights 20, a vibrating ring 22, a plurality of clips 24, speakers and microphone 26, a back pacifier panel 28, and a USB charging port 30. Turning to FIG. 5, a front view of the smart pacifier 10 in the second form is conceptually illustrated. In contrast to the butterfly shape of the removable front pacifier panel 18 of the smart pacifier 10 in the first form, described above by reference to FIGS. 1-3, removable front pacifier panel 18 of the smart pacifier 10 in the second form has a circular shape, approximating the shape of a circle. In comparison to the configuration and layout of the plurality of lights 20 of the smart pacifier 10 in the first form, described above by reference to FIGS. 1-3, the smart pacifier 10 in the second form includes a different configuration and layout of the plurality of lights 20. Specifically, the plurality of lights 20 include six front panel lights in pairs of varying size and a light ring around the perimeter of the removable front pacifier panel 18 that approximates the shape of a circle, as opposed to a butterfly shaped perimeter for the light ring of the smart pacifier 10 in the first form. Furthermore, the speakers and microphone 26 of the smart pacifier 10 in the second form have two slots, which differs from the three-slot speakers and microphone 26 of the smart pacifier 10 in the first form described above by reference to FIGS. 1-3. Now referring to another view, FIG. 6 conceptually illustrates a side view of the smart pacifier 10 in the second form. As shown in this figure, the back pacifier panel 28 and the removable front pacifier panel 18 are flat with no curvature, differing from the slight curvature demonstrated in the butterfly design for the smart pacifier 10 in the first form described above by reference to FIGS. 1-3. Also, several components of the smart pacifier 10 in the second form are embedded within the assembly of the back pacifier panel 28 and the pacifier nipple 14, including at least the temperature and pressure sensor component assembly 16 and the oscillating circuit board (not shown in this figure, but which is described below, by reference to FIGS. 9 and 10). In some embodiments, the vibrating ring 22 is also embedded within the assembly of the back pacifier panel 28 and the pacifier nipple 14. In some other embodiments, and as shown in FIG. 6, the vibrating ring 22 is connected to an outer surface of the pacifier nipple 14 in connection with the back pacifier panel 28 and include circuit wires through the back pacifier panel 28 to the oscillating circuit board in order to actuate the vibrating ring 22 when vibration functions are performed by the smart pacifier 10 in the second form.

The smart pacifier of the present disclosure generally works by wirelessly allowing a human user (such as a parent) to interact with a baby/child using the smart pacifier, or to entertain, stimulate, play music to, speak to, read to, record, or otherwise perform functions while the baby/child is using the smart pacifier as he or she would use any conventional pacifier to soothe by sucking or simply having the smart pacifier nearby (whether sucking or not). The additional features allow the baby/child to be soothed in other situations and by other mechanisms, such as when the baby or child is teething (e.g., the smart pacifier can provide inside vibration that comforts the ridge of the gums in the baby's or child's mouth) or just being fussy (e.g., the smart pacifier can play music, read a story, or play a recorded audio of a parent or display a light show for visual stimulation, etc.).

Generally, features and functions of the smart pacifier 10 in the first form and the smart pacifier 10 in the second form perform in like fashion. While several of the descriptions and examples which follow are described by reference to the smart pacifier 10 in the first form, these descriptions and examples are to be understood as also applying to the smart pacifier 10 in the second form. Therefore, while the descriptions and examples which follow may refer to drawings of the smart pacifier 10 in the first form, the smart pacifier 10 is henceforth referred to as the "smart pacifier 10" with the understanding that the smart pacifier 10 can be in the first form, in the second form, or in any other similar form which a person of ordinary skill in the relevant art would appreciate.

In some embodiments, the smart pacifier 10 needs to be in operational mode to work. In some embodiments, the smart pacifier 10 includes a battery which provides power for operation. In some embodiments, the battery is a rechargeable battery that is charged via the USB charging port 30. In some embodiments, the rechargeable battery is one of multiple rechargeable batteries that are embedded within the removable front pacifier panel 18 behind the power toggle button 12 with wires connected to components of the smart pacifier 10 which require power to operate. Furthermore, the smart pacifier 10 needs to process commands wirelessly received from the smart computing device used by the parent in order to actuate the components that provide the stimulating features and functions of the smart pacifier 10. To this end, the smart pacifier 10 includes an oscillating circuit board, which is described further below, by reference to FIGS. 9 and 10.

To use the smart pacifier 10 of the present disclosure, parents can be out of sight of the baby/child and still be connected with them through the features, functions, and interactive options of the smart pacifier 10, while the smart pacifier 10 entertains the baby/child with lights, sounds, music, pre-recorded or live voices, vibrations, etc., which are controlled by the parent's interaction with the application when smart pacifier 10 is in the mouth of the baby/child. The smart pacifier 10 receives sensory input from the child through the pacifier nipple 14, such as pressure, temperature, and moisture, or other sensory input, and receives control input in real-time via the smart computing device control application, thereby allowing the smart pacifier 10 to check temperature and other internals of the baby/child and send alerts, e.g., an alert if the temperature is too high. Furthermore, any type of vibration sequences, light sequence, or sound sequence, individually or in combination, can be utilized to stimulate/comfort the baby/child. In some embodiments, feedback is then sent directly to the smart computing device on which the application is running and is stored for later updating and learning via artificial intelligence (AI) and programmatic learning software systems or modules. The smart pacifier 10 can be programmed to shut off at a certain drop in the level of sensory input or on a pre-programmed metric such as time or other metric and if the smart pacifier 10 is lost, it can be located using the smart computing device application.

When the smart pacifier 10 is connected at the USB charging port 30 to a power source via USB cable, or when the rechargeable batteries embedded within the removable front pacifier panel 18 are charged, a parent or other guardian may manually turn the smart pacifier 10 on (into operational mode), make some music selections, and manually turn the smart pacifier 10 off by following at least three steps: (i) pressing down once on the power toggle button 12, which, in some embodiments, also automatically turns on Bluetooth and automatically makes a connection to an available device, such as the parent's mobile device with the application; (ii) pressing the power toggle button 12 again to find pre-selected music to play for the baby/child; and (iii) powering off manually by pressing down on the power toggle button 12 for an extended hold (i.e., one second press and hold down). Other functions and features can be interactively selected from the application running on the computing device/mobile device of the parent or guardian. While the manual operating steps are available for the parent, it is understood that the smart pacifier 10 of the present disclosure also supports automatic power down when the smart pacifier 10 detects that the pacifier is not in use by the baby/child. In some embodiments, the automatic power down is determined by the oscillating circuit board processing information provided by one or more sensors to detect whether the pacifier is in use. Furthermore, manually selecting music to play through the smart pacifier 10 is only one of several functions, features, and interactive options available. Music can also be selected from the smart computing device used by the parent and wirelessly transmitted to the smart pacifier 10 to play through the audio speaker. In addition, several of the supported functions, features, and interactive options of the smart pacifier 10 are described next, by reference to FIGS. 7-11.

Figure 7:
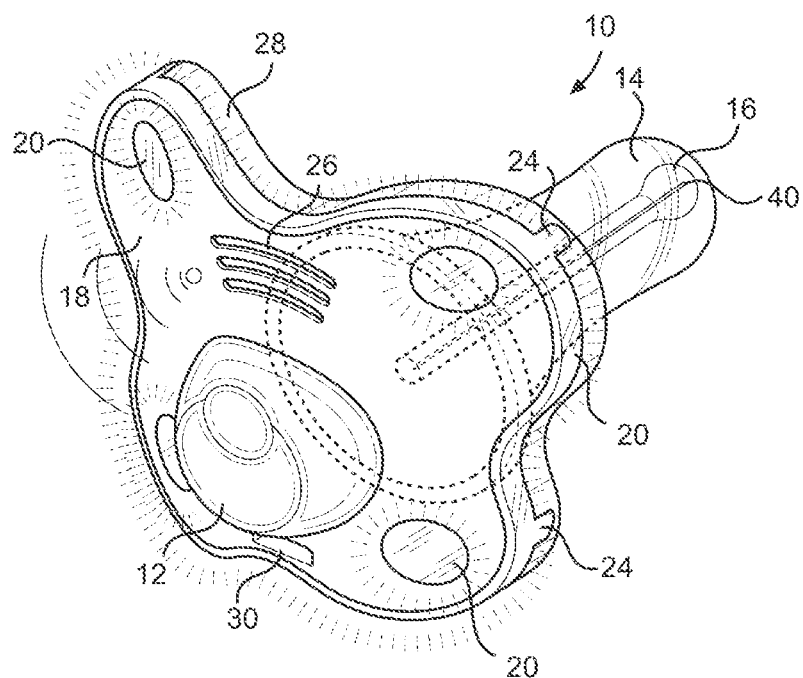
FIG. 7 conceptually illustrates a perspective view the smart pacifier in some embodiments while performing lighting and sound functions, and detecting usage by and temperature of a baby/child.
Figure 8:
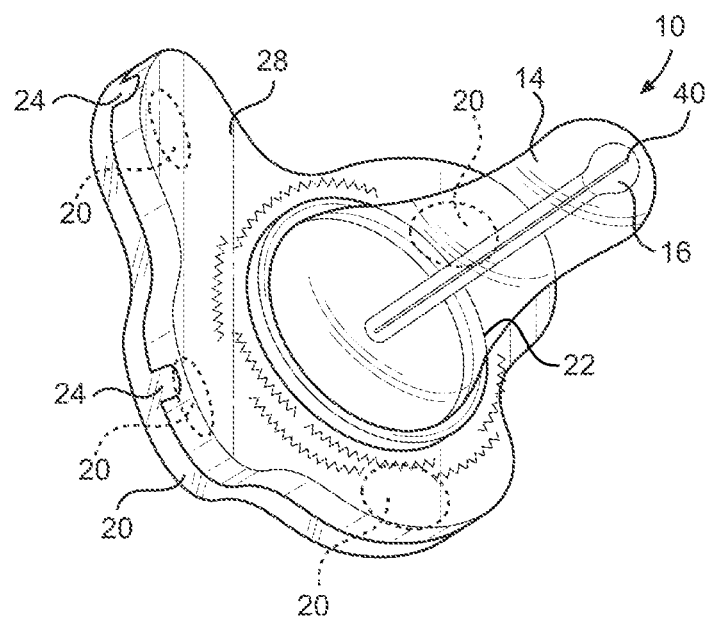
FIG. 8 conceptually illustrates a perspective view the smart pacifier with a removable front pacifier panel detached to demonstrate vibrations around a vibration ring and through a back pacifier panel of the smart pacifier while the smart pacifier is performing vibration functions in some embodiments.

By way of example, FIG. 7 conceptually illustrates a perspective view of the smart pacifier 10 while performing lighting and sound functions, and detecting usage by and temperature of a baby/child. Although not shown in this figure, the smart pacifier 10 employs an oscillating circuit board to process a command to start or stop shining the plurality of lights 20, to output audio sound through the speakers and microphone 26, to record sound at the microphone of the speakers and microphone 26, to measure temperature inside the mouth of the baby/child while sucking on the pacifier nipple 14, to process instructions and commands and generate notifications to send to the parent smart device, and to perform other functions, features, and interactive options.

As shown in FIG. 7, sound waves are emanating from an audio speaker of the speakers and microphone 26. In some embodiments, at least one audio speaker of the speakers and microphone 26 is a Bluetooth speaker. As such, the sound waves show emanating from the audio speaker in this figure demonstrates an audio stimulation function of the smart pacifier 10, as might be provided by playing music via Bluetooth speaker after a parent selects music songs from a wirelessly connected mobile smartphone that is interacting with the smart pacifier 10, or by playing an audio recording of a story or an audio recording of the parent's voice, or by interactively speaking to the baby/child from the mobile smartphone in realtime by wireless transmission of the parent's voice in realtime to the Bluetooth speaker 26 of the smart pacifier 10. Also shown in this figure are several sets of dashed lines emanating from the plurality of lights 20 of the smart pacifier 20. The lights 20 may shine different colors, such as yellow, pink, blue, green, etc., or any single or combination of colors that the plurality of lights 20 may be deployed as. In addition, the light ring of the plurality of lights 20 may display a light that travels around the perimeter of the removable front pacifier panel 18 along the light ring, circling until being turned off, or in synchronization with a light show being displayed with all of the plurality of lights 20. In some embodiments, the lights also turn on and off intermittently, so as to display a multi-colored light show for the baby/child. As noted above, the smart pacifier 10 of some embodiments includes automatic shut off. As shown in this figure, the smart pacifier includes the temperature and pressure sensor component assembly 16 with the high temperature alert device 40 embedded within the pacifier nipple 14. The temperature and pressure sensor component assembly 16 provides sensor-based decompression detection. By detecting the physical pressure of the baby, teething motions, and/or moisture presence, this decompression detection allows the smart pacifier 10 to automatically turn off once it is no longer being sucked on by the baby. In addition, the temperature and pressure sensor component assembly 16 with the high temperature alert device 40 detects the presence of temperature when the baby/child is sucking on the pacifier nipple 14. Specifically, the temperature and pressure sensor component assembly 16 measures temperature like a conventional baby thermometer inserted in a baby's mouth and triggers the high temperature alert device 40 to send an alert to the oscillating circuit board when the baby/child is running a high temperature. The alert causes the oscillating circuit board to generate an alert notification that is sent to the smart computing device being used by the parent or guardian. In this way, a parent/guardian is immediately notified of a high temperature when detected. For example, a threshold temperature level may be configured via the application and set to 101° Fahrenheit, such that the high temperature alert device 40 sends an alert to the oscillating circuit board when the temperature inside the mouth of the baby/child is measured at or above 101° F., thereby allowing for the high temperature alert notification to be created immediately by the oscillating circuit board (also referred to as an "oscillating processor") and sent to the smart computing device for display as an alert notification on the smart computing device screen (no matter what is currently being displayed) and/or displayed within the application used by the parent or guardian.

In some embodiments, the smart pacifier 10 includes at least one rechargeable battery that provides power to the plurality of the lights 20, the speakers and microphone 26, the temperature and pressure sensor component assembly 16 with the high temperature alert device 40, the oscillating circuit board, and other devices or components of the smart pacifier 10. In some embodiments, the oscillating circuit board also needs power and obtains the power from the battery. In some embodiments, the battery is one of multiple batteries. In some embodiments, one or more of the batteries are rechargeable batteries that are charged via the USB charging port 30. In some embodiments, batteries are embedded within the removable front pacifier panel 18 and are wired out to the components of the smart pacifier 10 which require power.

Another feature of the smart pacifier 10 is the ability to vibrate for teething babies or simply to provide another type of stimulation. By way of example, FIG. 8 conceptually illustrates a perspective view the smart pacifier 10 with the removable front pacifier panel 18 detached to demonstrate vibrations around a vibration ring 22 and through the back pacifier panel 28 (which may be opaque but is demonstrated in this example as transparent so as to illustrate overall detail of the smart pacifier 10 from front to back, and conceptually illustrate vibrations of the vibration ring 22). Specifically, the vibration ring 22 operates to keep the baby calm and help with teething. In some embodiments, the vibration ring 22 that can be programmed for various levels of vibration and rhythms. The vibrations are conceptually illustrated in this figure as semi-circular sketch lines partially surrounding the vibration ring 22. Like other functions and features of the smart pacifier 10, the vibrating function can be started remotely by the parent or guardian interacting with the application running on the smart computing device being used (e.g., smartphone or other mobile computing device, desktop computer, laptop computer, etc.). Although not shown in this figure, the smart pacifier 10 needs the oscillating circuit board to process a command to start or stop performing vibrations and also needs power via one or more charged batteries within the removable front pacifier panel 18 to actuate the vibration ring 22.

In essence, the smart pacifier 10 is entertaining and calming for the baby/child. A parent can record his or her voice for playback to the baby/child through the audio speaker of the smart pacifier 10. Alternatively, the parent or a guardian can wirelessly and remotely read stories for the baby/child in realtime, or record stories which the parent/guardian has previously read for playback. The smart pacifier 10 can play music and the plurality of lights 20 can be synchronized by the oscillating processor to be rhythmically in tune with the music. Since there is embedded instruction processing and intelligent decision-making via the oscillating process, and due to its having onboard wireless connectivity, all of these functions, features, and interaction options can be controlled by way of an application running on a wireless-capable computing device, such as a smartphone or other mobile computing device (e.g., tablet computing device), or a desktop or laptop computer with a Bluetooth transceiver module, or for an unconnected (no wireless) version, any computing device that can run the application and connect to the smart pacifier 10 through a direct cable link, such as a USB cable or other wired connectivity, as is described further below, by reference to FIG. 11.

Generally, the features, functions, and interactive options provided by the smart pacifier 10 are supported by logic-based instruction sets processed via the processor of the oscillating circuit board. These various features, functions, and interactive options, as well as interconnection between these features, functions, and interactive options provide input to the oscillating circuit board via sensors and sensitive device modules, which capture information about the sucking pressure of the baby/child, the temperature of the inside of the mouth of the baby/child or other environmental factors, such as thermal input and potential moisture input, and provide such information to the oscillating circuit board for the oscillating processor to determine whether the baby/child is sucking on the smart pacifier 10, noting any occurrence of high temperature, and relaying that information on to the smart computing device application for the parent to review. Time-delay circuits can be configured and set for the oscillating circuit board, primarily, but not exclusively, controlled through the smart computing device application to automatically shut off the power (as described above) to the smart pacifier 10 and its battery to conserve battery life.

Figure 9:
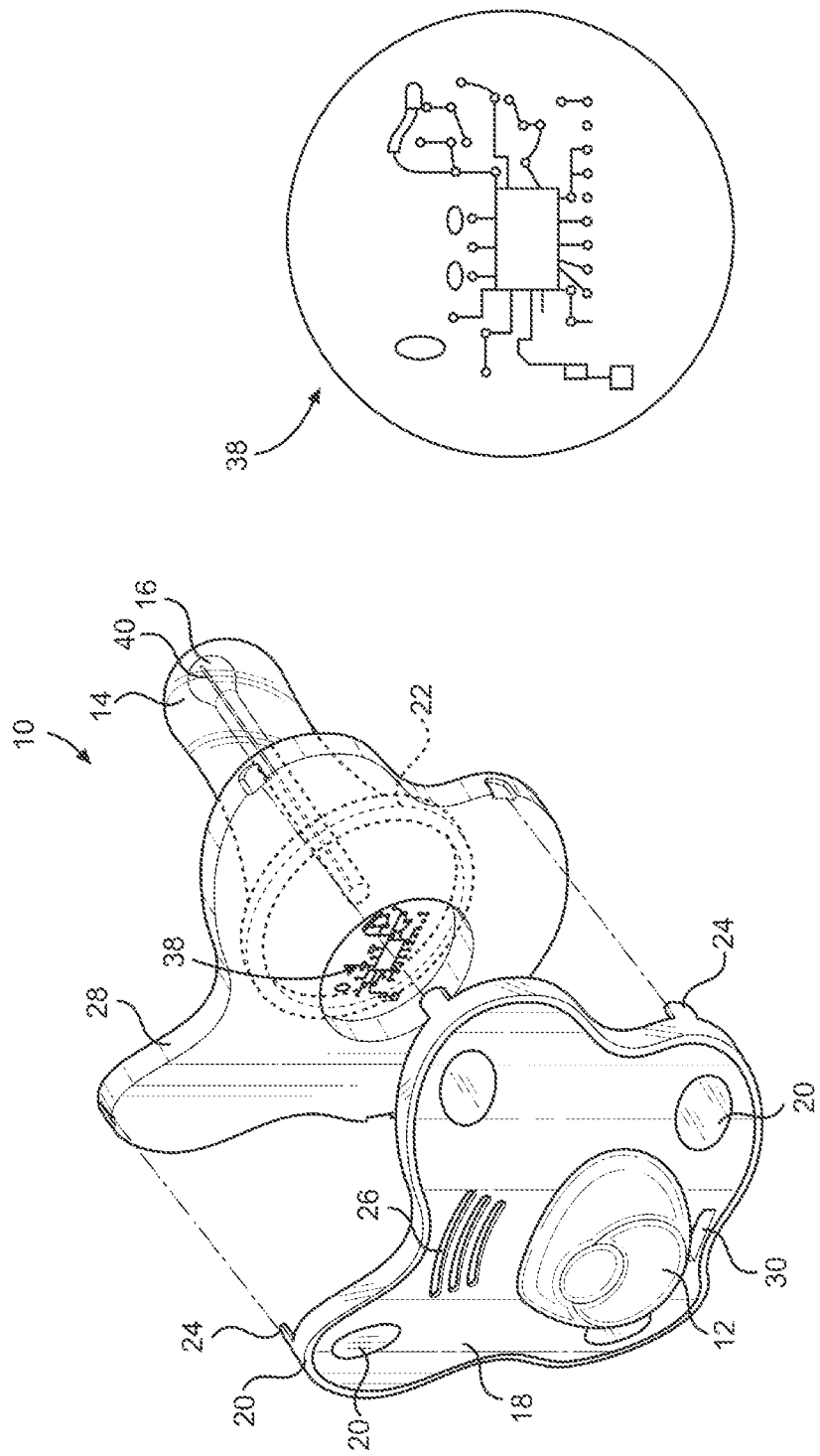
FIG. 9 conceptually illustrates a perspective, exploded view the smart pacifier with the removable front pacifier panel detached to show an oscillating circuit board embedded in the smart pacifier in some embodiments.

Turning now to another example, FIG. 9 conceptually illustrates a perspective, exploded view the smart pacifier 10 with the removable front pacifier panel 18 detached to show a location in the smart pacifier 10 of an oscillating circuit board 38, which is embedded in the removable front pacifier panel 18, but which is shown in this figure as appearing within a carve out section within the back pacifier panel 28. As shown in this figure, the removable front pacifier panel 18 is detached from the back pacifier panel 28 of the smart pacifier 10 by releasing the plurality of clips 24 and pulling the removable front pacifier panel 18 apart from the back pacifier panel 28 of the smart pacifier 10. Also, while not shown in this figure, detaching the removable front pacifier panel 18 from the back pacifier panel 28 of the smart pacifier 10 reveals wires, batteries, and other embedded components embedded within the removable front pacifier panel 18 of the smart pacifier 10.

Figure 10:
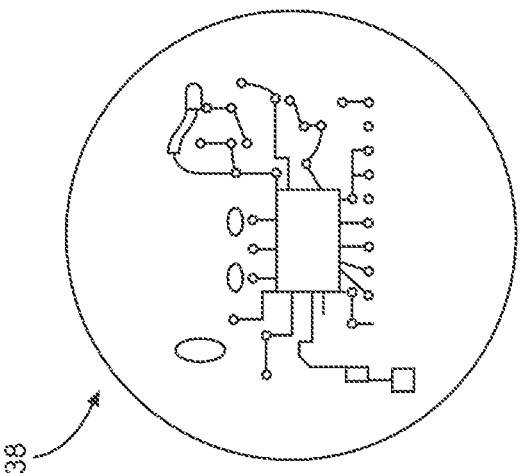
FIG. 10 conceptually illustrates a front view of the oscillating circuit board in some embodiments.

By way of example, FIG. 10 conceptually illustrates a front view of the oscillating circuit board 38. As shown in this example, the oscillating circuit board 38 includes several connected modules and components. At least one of the components wired into of the oscillating circuit board 38 is a wireless transceiver module. In some embodiments, the wireless transceiver module is a Bluetooth transceiver module. In some embodiments, a WiFi network communication module is wired into the oscillating circuit board 38. In some embodiments, an oscillating processor is a central component of the oscillating circuit board 38 and provides runtime instruction set processing and information routing between the sensors and devices of the smart pacifier 10 and the oscillating circuit board 38, as well as information routing between any smart computing device connected to the smart pacifier 10 while running the application. In some embodiments, the oscillating circuit board 38 includes a paired device management module that is able to manage music and audio selections, temperature threshold settings, and other configurable parameter settings of a first connected smart computing device and transfer the managed music and audio selections, temperature threshold settings, and other configurable parameter settings to a second smart computing device that connects to the smart pacifier 10. In this way, two smart computing devices, one for each of two parents, can connect simultaneously to the smart pacifier 10 and enjoy all the features, functions, and interactive options together, or one parent or guardian can choose to transfer connection to another parent or guardian without losing any of the configuration settings of the smart pacifier 10, such as when a parent configures the smart pacifier 10 for use by a baby/child and the parent then transfers the smart pacifier 10 connection over to a smart computing device of a baby sitter or other qualified guardian.

In some embodiments, several circuit modules of the oscillating circuit board 38 are internally programmed and configured. In some embodiments, the internally programmed circuit modules of the oscillating circuit board 38 are primarily controlled and set through parameterized configuration setting in the application running on the smart computing device used by the parent. For instance, the sensors within the smart pacifier 10 provide sensory data that is captured by the sensors when the baby/child uses the smart pacifier 10 (e.g., capturing pressure and environmental data, such as thermal input and moisture input, among others), and the circuit modules of the oscillating circuit board 38 are programmed and configured to receive the sensory data and respond in any of several programmatic ways, depending on the type of sensory data and the desires of the parent with respect to how the features, function, and interactive options are triggered for the smart pacifier 10. In some embodiments, time-delay circuits are set for the oscillating circuit board 38 to automatically shut off the power to the smart pacifier 10 and its battery to conserve battery life. In some embodiments, setting the time-delay circuits for automatic shut off of the power is primarily, but not exclusively, controlled through the application on the smart computing device.

In some embodiments, time-delay circuits are set for the oscillating circuit board 38 to automatically shut off the power to the smart pacifier 10 and its battery to conserve battery life. In some embodiments, setting the time-delay circuits for automatic shut off of the power is primarily, but not exclusively, controlled through the application on the smart computing device.

In some embodiments, the smart pacifier 10 includes a global positioning system (GPS) chip that receives location information from GPS satellites and transmits its location to the application of any smart computing device that is paired to the smart pacifier 10 and configured to allow user interaction with the smart pacifier 10 via the application. In this way, the smart pacifier 10 can easily be located if dropped, lost, or otherwise misplaced.

Figure 11:
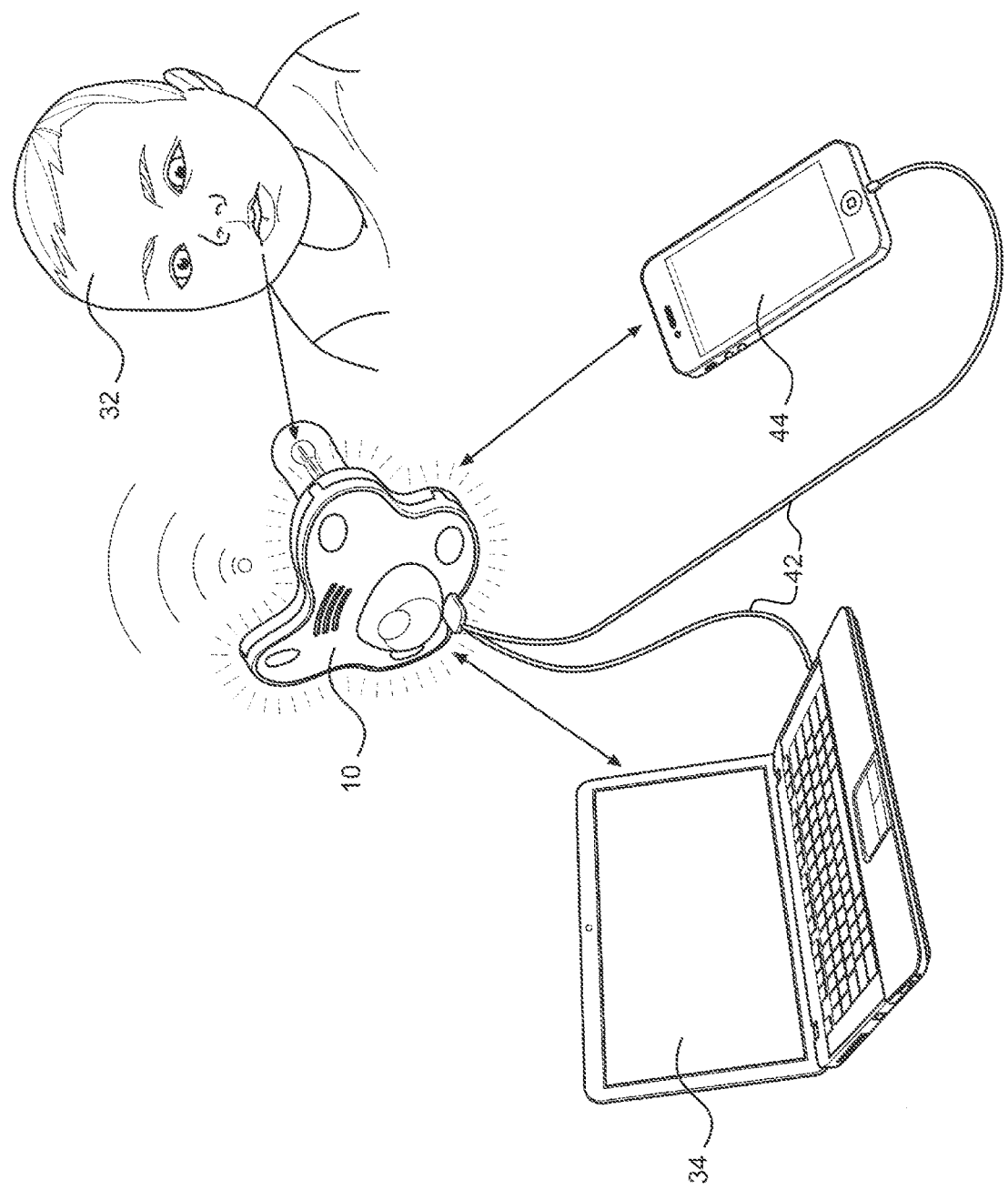
FIG. 11 conceptually illustrates a diagrammatic view of the smart pacifier in relationship to a baby and in connection with a laptop computing device and a smart mobile device on which an application runs to allow a human user to interact with the smart pacifier in some embodiments.

By way of example, FIG. 11 conceptually illustrates a diagrammatic view of the smart pacifier 10 in relationship to a baby 32 and in connection, by either or both of a wireless Bluetooth connection or a USB cable 42, with a laptop computing devices 34 and a smart mobile device 44 on which the application runs to allow a human user, such as a parent or guardian, to interact with the smart pacifier 10. In some cases, the USB cable 42 may connect from the USB charge port 30 of the smart pacifier 10 into a power/data communication port of the smart computing device (whether the laptop computing device 34 or the smart mobile device 44) to charge the rechargeable battery of the smart pacifier 10, while maintaining a wireless (Bluetooth) data connection between the smart computing device (again, one or both of the laptop computing device 34 and the smart mobile device 44) and the smart pacifier 10. In some other cases, the USB cable 42 may be used for power recharging the battery of the smart pacifier 10 (connecting from the USB charge port 30 of the smart pacifier 10 into a power/data communication port of the smart computing device) and for connecting via wired USB cable 42 connection between either smart computing device or both smart computing devices and the smart pacifier 10.

In some embodiments, the battery of the smart pacifier 10 connects into a charging circuit of the smart pacifier 10 to both provide internal power to the components of the smart pacifier 10 and to recharge the battery when low or spent. In some embodiments, a charging routine of the charging circuit determines when the battery is fully recharged. In some embodiments, programming that runs on the oscillating processor of the oscillating circuit board determines when the charging routine is completed and the battery is recharged and changes a graphical indicator in a graphical user interface of the application that is visually output onto a screen of the smart computing device when the application is running. In some embodiments, the graphical indicator indicates an amount of remaining battery charge. In some embodiments, the programming also changes an indicator light of the smart pacifier 10 to indicate a battery charge status of full charge or not fully charged. In some embodiments, the indicator light displays different light colors to indicate an amount of remaining battery charge. In some embodiments, the graphical indicator and the indicator light indicate battery status when the USB cable 42 is connected to the USB charge port 30 of the smart pacifier 10 and a USB power source. For instance, the USB cable 42 may be connected to the laptop computing device 34, the smart mobile device 44, another type of smart computing device, or a USB wall socket/charger. In some embodiments, the graphical indicator and the indicator light indicate battery status when the smart pacifier 10 is wirelessly connected to the smart computing device without any USB cable 42 connection to the USB charge port 30 of the smart pacifier 10. In this way, the graphical indicator of the application or the indicator light of the smart pacifier 10 are able to notify/prompt the user of the smart computing device to recharge the smart pacifier 10 battery when low in remaining charge, which can be done either through direct plugging in for recharging or wireless recharging (such as inductive charging).

To make the smart pacifier 10 of the present disclosure, a mechanical engineer, electrical engineer, biomedical engineer, and/or a computer engineer, as well as various support engineers work together in teams or individually and combine all skills to bring the smart pacifier 10 to fruition. From a manufacturing perspective, the smart pacifier 10 is made by a tool die casting or other such process to create the external surface components including the power toggle button 12 made of a hard outer covering material, the pacifier nipple 14 made of silicone or other soft and durable baby-safe material, the removable front pacifier panel 18 made of the same or similar hard outer covering material, and the back pacifier panel 28 made of the same or similar hard outer covering material, along with integrating the speakers and microphone 26, the plurality of lights 20 (and including the battery indicator light), and the USB charge port 30 within the removable front pacifier panel 18 to be exposed along the surface of the removable front pacifier panel 18, while embedding the temperature and pressure sensor component assembly 16 with the high temperature alert device 40 within the pacifier nipple 14 and into the back pacifier panel 28, as well as embedding the vibration ring 22, the oscillating circuit board 38, the wireless/Bluetooth module, the GPS chip, the battery/batteries, the charging circuit, WiFi networking module/chip, and internal wiring within the removable front pacifier panel 18.

While the temperature and pressure sensor component assembly 16 and the high temperature alert device 40 are housed within the pacifier nipple 14, the other embedded components are not housed within the pacifier nipple 14, but instead are embedded into the removable front pacifier panel 18, such that the smart pacifier 10 can still be used by a baby/child when the removable front pacifier panel 18 is detached and removed. Also, without the computer/electro-mechanical parts and components present, it is possible to change the pacifier nipple 14 or replace one or more of the embedded components or electro-mechanical parts within the removable front pacifier panel 18.

The back pacifier panel 28 of the smart pacifier 10 is a single unit that is assembled prior to connection to the pacifier nipple 14. Internal to the pacifier nipple 14, the temperature and pressure sensor component assembly 16 with the high temperature alert device 40 are designed for placement within the pacifier nipple 14 in a way that does not deform the shape of the pacifier nipple 14. In some embodiments, a gyro is inserted sufficiently into the pacifier nipple 14 to provide vibrations. In some embodiments, the gyro enhances the vibration ring 22, which is embedded within the back pacifier panel 28 in some embodiments, while being disposed along an outer edge of the back pacifier panel 28 in connection with the pacifier nipple 14 in some other embodiments. In this way, the vibration ring 22, by itself or in combination with the gyro, are able to provide the teething stimulation function for comforting the baby/child.

In addition, the removable front pacifier panel 18 can be disconnected, leaving the back pacifier panel 28 and pacifier nipple 14 of the smart pacifier 10 to be used as a conventional pacifier without the electro-mechanical components. This permits change/replacement of various parts of the control mechanisms or replacement of the pacifier nipple.

Many of the above-described features and applications are implemented as software application processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "application", and "mobile app" are meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 12:
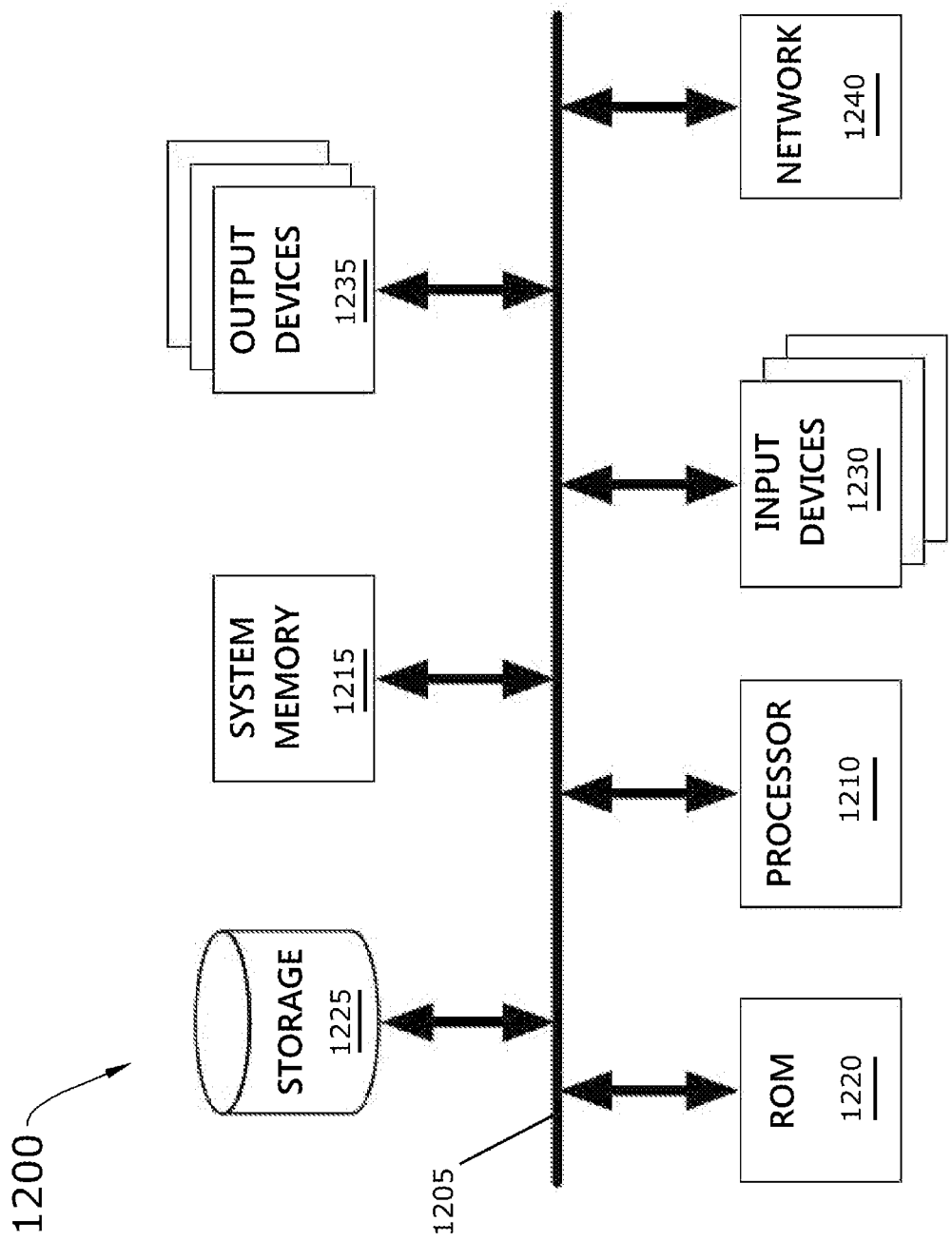
FIG. 12 conceptually illustrates an electronic system with which some embodiments of the invention are implemented.

FIG. 12 conceptually illustrates an electronic system 1200 with which some embodiments of the invention are implemented. The electronic system 1200 may be a computer (desktop computer, laptop computer, etc.), phone (cell phone, mobile phone, smartphone, etc.), wireless PDA (iPod, tablet computing device, other handheld computing device, etc.), or any other sort of electronic device or computing device. Such an electronic system includes various types of computer readable media and interfaces for various other types of computer readable media. Electronic system 1200 includes a bus 1205, processing unit(s) 1210, a system memory 1215, a read-only 1220, a permanent storage device 1225, input devices 1230, output devices 1235, and a network 1240.

The bus 1205 collectively represents all system, peripheral, and chipset buses that communicatively connect the numerous internal devices of the electronic system 1200. For instance, the bus 1205 communicatively connects the processing unit(s) 1210 with the read-only 1220, the system memory 1215, and the permanent storage device 1225.

From these various memory units, the processing unit(s) 1210 retrieves instructions to execute and data to process in order to execute the processes of the invention. The processing unit(s) may be a single processor or a multi-core processor in different embodiments.

The read-only-memory (ROM) 1220 stores static data and instructions that are needed by the processing unit(s) 1210 and other modules of the electronic system. The permanent storage device 1225, on the other hand, is a read-and-write memory device. This device is a non-volatile memory unit that stores instructions and data even when the electronic system 1200 is off. Some embodiments of the invention use a mass-storage device (such as a magnetic or optical disk and its corresponding disk drive) as the permanent storage device 1225.

Other embodiments use a removable storage device (such as a floppy disk or a flash drive) as the permanent storage device 1225. Like the permanent storage device 1225, the system memory 1215 is a read-and-write memory device. However, unlike storage device 1225, the system memory 1215 is a volatile read-and-write memory, such as a random access memory. The system memory 1215 stores some of the instructions and data that the processor needs at runtime. In some embodiments, the invention's processes are stored in the system memory 1215, the permanent storage device 1225, and/or the read-only 1220. For example, the various memory units include instructions for processing appearance alterations of displayable characters in accordance with some embodiments. From these various memory units, the processing unit(s) 1210 retrieves instructions to execute and data to process in order to execute the processes of some embodiments.

The bus 1205 also connects to the input and output devices 1230 and 1235. The input devices enable the user to communicate information and select commands to the electronic system. The input devices 1230 include alphanumeric keyboards and pointing devices (also called "cursor control devices"). The output devices 1235 display images generated by the electronic system 1200. The output devices 1235 include printers and display devices, such as cathode ray tubes (CRT) or liquid crystal displays (LCD). Some embodiments include devices such as a touchscreen that functions as both input and output devices.

Finally, as shown in FIG. 12, bus 1205 also couples electronic system 1200 to a network 1240 through a network adapter (not shown). In this manner, the computer can be a part of a network of computers (such as a local area network ("LAN"), a wide area network ("WAN"), or an intranet), or a network of networks (such as the Internet). Any or all components of electronic system 1200 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, flash memory (e.g., SD cards, mini-SD cards, micro-SD cards, etc.), magnetic and/or solid state hard drives, optical media, or other media. The computer-readable media may store a computer program or application (also referred to as "mobile app") that is executable by at least one processing unit and includes sets of instructions for performing various operations. Examples of computer programs, applications, mobile apps, or computer code include machine code, such as is produced by a compiler, and files including higher-level code that are executed by a computer, a mobile computing device, an electronic component, or a microprocessor using an interpreter.

While the invention has been described with reference to numerous specific details, one of ordinary skill in the art will recognize that the invention can be embodied in other specific forms without departing from the spirit of the invention. For instance, FIGS. 1-3 and FIGS. 4-6 conceptually illustrate different forms of the smart pacifier. However, the smart pacifier may appear in other specific forms in different embodiments. Thus, one of ordinary skill in the art would understand that the invention is not to be limited by the foregoing illustrative details, but rather is to be defined by the appended claims.

I claim:

1. A smart pacifier comprising:
    a pacifier nipple inserted into a mouth of a child to soothe the child;
    a back pacifier panel to which the pacifier nipple is connected and which limits a distance inside the mouth of the child in which the nipple is inserted;
    a removable front pacifier panel that attaches to and detaches from the back pacifier panel;
    a wireless transceiver module embedded within the removable front pacifier panel, said wireless transceiver module configured to send and receive wireless data communication from a computing device operated by a parent of the child;
    a plurality of lights that are disposed along a front surface of the removable front pacifier panel, said plurality of lights configured to light up to stimulate the child when a remote light command to turn on the plurality of lights is received at the wireless transceiver module from the computing device operated by the parent of the child; and
    an audio speaker that is disposed along the front surface of the removable front pacifier panel, said audio speaker configured to aurally output sound when a remote sound command to play a sound is received at the wireless transceiver module from the computing device operated by the parent of the child.

2. The smart pacifier of claim 1, wherein the wireless transceiver module comprises a Bluetooth wireless communication module.

3. The smart pacifier of claim 2, wherein the audio speaker comprises a Bluetooth speaker.

4. The smart pacifier of claim 3, wherein the sound comprises music selected by the parent at the computing device, wherein the audio speaker aurally outputs sound by playing the selected music.

5. The smart pacifier of claim 1 further comprising a vibration ring that is configured to vibrate the pacifier nipple to provide teething comfort to the child.

6. The smart pacifier of claim 5 further comprising a temperature and pressure sensor component assembly that fits within the pacifier nipple, said temperature and pressure sensor component assembly comprising a pressure sensor, a thermal sensor, and a high temperature alert device embedded within the pacifier nipple.

7. The smart pacifier of claim 6, wherein pressure sensor provides sensor-based decompression detection based on one of more of physical pressure of the mouth of the child, teething motions of the child, and moisture presence.

8. The smart pacifier of claim 7, wherein the thermal sensor provides thermal temperature data to detect internal temperature of the child when decompression is detected by the child sucking the pacifier nipple of the smart pacifier.

9. The smart pacifier of claim 8, wherein the high temperature alert device triggers a high temperature alert when the detected internal temperature of the child is above a threshold temperature.

10. The smart pacifier of claim 9 further comprising an oscillating circuit board that is embedded within the removable front pacifier panel and includes circuitry that connects to the wireless transceiver module, the plurality of lights, the audio speaker, the vibration ring, and the temperature and pressure sensor component assembly, wherein the oscillating circuit board is configured to (i) process commands received at the wireless transceiver module from the computing device operated by the parent, (ii) trigger operation of the plurality of lights, the audio speaker, the vibration ring, and the temperature and pressure sensor, (iii) send a high temperature alert to the computing device operated by the parent of the child when the internal temperature of the child exceeds the threshold temperature, and (iv) automatically turn off power of the smart pacifier when a threshold amount of time passes in which no decompression is detected.

* * * * *